United States Patent [19]

Schoen et al.

[11] Patent Number: 5,324,732
[45] Date of Patent: Jun. 28, 1994

[54] CRYSTALLINE FUMARIC ACID SALTS OF 9,9-ALKYLENE-3,7-DIAZABICYCLONONANE COMPOUNDS AND PHARMACEUTICAL COMPOSITIONS CONTAINING THEM

[75] Inventors: Uwe Schoen, Burgdorf; Walter Heitmann, Burgwedel; Uwe Maetzel, Burgdorf, all of Fed. Rep. of Germany

[73] Assignee: Kali-Chemie Pharma GmbH, Hanover, Fed. Rep. of Germany

[21] Appl. No.: 980,177

[22] Filed: Nov. 23, 1992

[30] Foreign Application Priority Data

Dec. 3, 1991 [DE] Fed. Rep. of Germany ....... 4139763

[51] Int. Cl.$^5$ .................. A61K 31/445; C07D 451/14
[52] U.S. Cl. ........................................ 514/278; 546/18
[58] Field of Search ........................... 546/18; 514/278

[56] References Cited

U.S. PATENT DOCUMENTS 4,550,112 10/1985 Schoen et al. ............... 514/278
5,164,401 11/1992 Burow et al. ................ 514/300

FOREIGN PATENT DOCUMENTS 103833 3/1984 European Pat. Off. .
76338 6/1988 Finland .

OTHER PUBLICATIONS

European Pharmacopoeia, Second Edition, V.3.5.6.–1 1992.

*Primary Examiner*—Mukund J. Shah
*Assistant Examiner*—Y. N. Gupta
*Attorney, Agent, or Firm*—Evenson, McKeown, Edwards & Lenahan

[57] ABSTRACT

1.5 Fumaric acid salts of N,N'-di-lower alkyl-substituted 9,9-alkylene-3,7-diazabicyclo[3.3.1 ]nonanes and a process for obtaining them in stoichiometrically pure and virtually non-hygroscopic form.

7 Claims, No Drawings

CRYSTALLINE FUMARIC ACID SALTS OF 9,9-ALKYLENE-3,7-DIAZABICYCLONONANE COMPOUNDS AND PHARMACEUTICAL COMPOSITIONS CONTAINING THEM

BACKGROUND OF THE INVENTION

The present invention relates to novel crystalline fumaric acid salts of N,N'-disubstituted 9,9-alkylene-3,7-diazabicyclo[3.3.1]nonane compounds corresponding to the general formula I

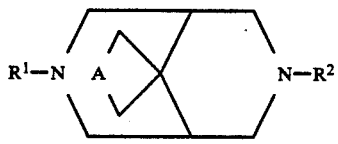

in which A denotes an alkylene chain of 4–5 carbon atoms and $R^1$ and $R^2$ independently of one another each denote a straight-chain or branched alkyl group of 3–4 carbon atoms or the cyclopropylmethyl group.

9,9-Alkylene-3,7-diazabicyclononane compounds of formula I and their pharmacological activities are known from published European Patent No. EP 103,833 and the corrosponding U.S. Pat. No. 4,550,112, and Finnish Patent No. FI 76,338. compounds of formula I are a sub-group of the 9,9N,N'-tetrasubstituted 3,7-diazabicyclo[3.3.1]-nonane compounds described in the aforementioned patent specifications and can be prepared by the methods described therein. The aforementioned patent specifications disclose that the compounds have useful cardio-active properties, particularly oxygen-saving effects and effects on the heart rate and heart rhythm, and are distinguished by a high physiological tolerance. Thus, the compounds show a satisfactory antiarrhythmic action even at low doses. Moreover, the undesired negative effect on the contractile power of the heart is extremely low; i.e. the compounds have a particularly favorable ratio of antiarrhythmic or the refractory period of the heart prolonging activities, to negative inotropic secondary activities.

Moreover, it is described in Burow et al., U.S. Pat. No. 5,164,401, the compounds also have a pronounced diuretic effect with a favorable ratio between sodium and potassium excretion.

Salts of compounds of formula I described in Finnish Patent No. FI 76,338, include the dihydrogentartrate, and in copending U.S. patent application Ser. No. 07/714,886, the dihydrogentartrate and the dihydrochloride of N,N'-dicyclopropylmethyl-9,9-tetramethylene-3,7-diazabicyclo[3.3.1 ]-nonane and the dihydrogentartrate and the dihydrogenfumarate of N-isobutyl-N'-isopropyl-9,9-pentamethylene-3,7-diazabicyclo[3.3.1]nonane.

The salts of the compounds of the formula I used in the past have the disadvantage that they are not obtained in crystalline form. Instead, they are obtained in amorphous form as, for example, the hydrogentartrates, and/or are strongly hygroscopic as, for example, the hydrochlorides. Because of varying solvent contents in salts of this type, it is not possible without special precautionary measures to assure a constant stoichiometric composition and a constant bioavailability.

SUMMARY OF THE INVENTION

It was the object of the invention to provide crystalline and stoichiometrically homogeneous, virtually solvate-free salts of 9,9 ,N,N'-tetrasubstituted 3,7-diazabicyclo[3.3.1 ]nonane compounds.

Another object of the invention is to provide salts of 9,9,N,N'-tetrasubstituted 3,7-diazabicyclo[3.3.1]nonane compounds which are non-hygroscopic.

It was also an object of the invention to provide salts of 9,9,N,N'-tetrasubstituted 3,7-diazabicyclo[3.3.1]nonane compounds which exhibit adequate water solubility for convenient use in aqueous formulations.

These and other objects of the invention are achieved by providing a fumaric acid salt of a 9,9-alkylene-3,7diazabicyclo[3.3.1]nonane compound corresponding to the formula I

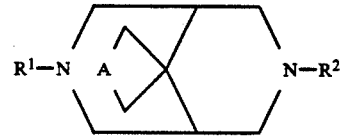

wherein
A denotes an alkylene chain of 4–5 carbon atoms, and $R^1$ and $R^2$ independently of one another each denote a straight-chain or branched alkyl group of 3–4 carbon atoms or the cyclopropylmethyl group;
said salt containing 1.5 moles of fumaric acid per mole of compound of formula I.

According to a further preferred aspect of the invention, the objects are achieved by providing a process for preparing a fumaric acid salt of a 9,9-alkylene-3,7-diazabicyclo[3.3.1]nonane compound corresponding to the formula I

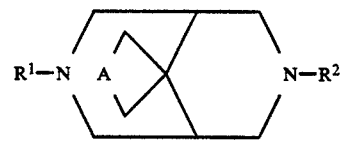

wherein
A denotes an alkylene chain of 4–5 carbon atoms, and $R^1$ and $R^2$ independently of one another each denote a straight-chain or branched alkyl group of 3–4 carbon atoms or the cyclopropylmethyl group;
said salt containing 1.5 moles of fumaric acid per mole of said compound of formula I;
said process comprising
admixing
a solution of said compound of formula I and of an at least 1.5-fold molar amount of fumaric acid in a lower alcohol, and
a less polar organic solvent,
whereby a salt containing 1.5 moles of fumaric acid per mole of said compound of formula I crystallizes, and separating the crystallized salt from the solution.

DETAILED DESCRIPTION OF PREFERRED EMBODIMENTS

It has now been found that such 9,9,N,N'-tetra-substituted 3,7-diazabicyclo[3.3.1]nonane compounds, which are substituted in the 9,9-position by an alkylene chain of 4–5 carbon atoms, i.e. have a spiro structure, and are substituted on each of the two nitrogen atoms by an alkyl group of 3-4 carbon atoms or by cyclopropylmethyl, can form stable crystalline salts with fumaric acid in a molar ratio of 1:1.5.

The invention accordingly relates to fumaric acid salts of 9,9-alkylene-3,7-diazabicyclo[3.3.1]nonane compounds of the general formula I

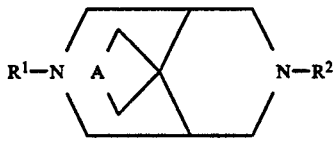

in which A denotes an alkylene chain of 4-5 carbon atoms and $R^1$ and $R^2$ independently of one another each denote a straight-chain or branched alkyl group of 3-4 carbon atoms or the cyclopropylmethyl group, which contain 1.5 moles of fumaric acid per mole of base of the formula I.

Compounds of the formula I which may be employed in the invention include, in particular, N-isobutyl-N'-isopropyl-9,9-pentamethylene-3,7-diazabicyclo[3.3.1-]nonane (generic name=bertosamil) and N,N'-dicyclopropylmethyl-9,9tetramethylene-3,7-diazabicyclo[3.3.1-]nonane (generic name =tedisamil).

The sesquihydrogenfumarates of the compounds of the formula I according to the invention are prepared by mixing a solution containing the base of formula I and an at least 1.5-fold molar amount of fumaric acid in a lower alcohol with a less polar organic solvent, whereby the salt containing 1.5 moles of fumaric acid per mole of base of formula I is crystallized, and then separating the crystallized salt.

Suitable lower alcohols include, for example, methanol, ethanol or isopropanol, in particular methanol or ethanol. Suitable solvents which are less polar compared to the lower alcohol include lower aliphatic ketones, in particular acetone, or lower aliphatic open-chain ethers, in particular diethyl ether.

Advantageously, a 1.5 molar to 2 molar amount of fumaric acid is employed in relation to the base of formula I. If an excess of fumaric acid is used, it may possibly be necessary, in order to remove dihydrogenfumarate salt by-products, to recrystallize the precipitated salt several times until a constant melting point is obtained. The concentration of the base of the formula I in the alcoholic solution can be varied in any desired manner depending on the solubility of the compound, the dissolution temperature and the batch quantity. For example, the base concentration may lie in the range from 3 to 50 moles per liter.

The volume ratio of alcoholic solution and less polar solvent can vary depending on the concentration of the compound of formula I in the alcoholic solution, on the solubility of the 1.5 hydrogenfumarate of the compound of formula I to be crystallized, on the nature of the less polar solvent, and on the volume of less polar solvent. However, the volume of the less polar solvent should always be a multiple of the volume of the alcoholic solution. For example, a volume ratio of alcoholic solution to less polar solvent which proves advantageous is in the range from 1:15 to 1:25, in particular about 1:20. To mix the alcoholic solution with the less polar solvent, the less polar solvent can either be added to the alcoholic solution, or the alcoholic solution can be added to the less polar solvent. For example, the alcoholic solution may be gradually added dropwise to the less polar solvent. If desired, the resulting mixture can be heated under reflux, for example up to the boiling point of the reaction mixture, to form a homogeneous solution. The 1.5 hydrogenfumarate of the compound of formula I is then allowed to crystallize, preferably with cooling of the mixture, for example at temperatures between room temperature and 0° C.

The crystallized salts can be separated from the mother liquor in a known manner, for example by filtration, optionally under reduced pressure, and then dried at slightly elevated temperatures, for example at temperatures between 40 and 65° C. preferably in a vacuum dryer.

The following examples are intended to illustrate the invention in further detail without, however, limiting its scope. The melting ranges given in the following examples were determined by differential scanning calorimetry, abbreviated "DSC" using a Perkin Elmer DSC 7 apparatus The peaks of the energy curve reflecting the melting range were determined at a heating rate of 10° C./minute. The weight loss on drying given in the examples was determined by thermogravimetric analysis, abbreviated "TGA", using a Perkin-Elmer TGA 7 apparatus at a heating rate of 20° C. per minute.

EXAMPLE 1

Preparation of
N-isobutyl-N'-isopropyl-9,9-pentamethylene-3,7-diazabicyclo [3.3.1]nonane-1.5 hydrogen-fumarate
(=bertosamil-1.5 hydrogenfumarate)

6.2 kg (=11.8 moles) of bertosamil dihydrogenfumarate were dissolved in 2.6 l of methanol at a temperature of 50° C. 52 l of acetone were then added to the solution and the reaction mixture was refluxed for 7 hours. The reaction mixture was then slowly cooled to room temperature. The mother liquor was filtered off from the precipitate formed through a suction filter, and this precipitate was washed with 1 l of acetone and dried in a drying oven at 50° C. 3.6 kg of crude crystals having a melting point of 90 to 95° C were obtained. The crude crystals were dissolved again in 2 liters of methanol at 50° C. and 42 liters of acetone were added to the solution. The reaction mixture was slowly cooled to room temperature with stirring. The precipitate which formed was separated from the mother liquor by suction filtration, washed with 1 liter of acetone, and dried in a drying oven at 50° C. 2.82 kg of bertosamil-1.5 hydrogenfumarate having a melting range of 104.5 to 107.4° C. were obtained. This melting range did not change on further recrystallization from methanol/acetone. The base:acid ratio determined by titration was 1:1.5. Thermogravimetric analysis showed no weight loss on drying.

EXAMPLE 2

Preparation of
N,N'-dicyclopropylmethyl-9,9-tetramethylene-3,7-diazabicyclo [3.3.1]nonane 1,5 hydrogenfumarate
(=tedisamil 1.5 hydrogenfumarate)

3.7 g (=0.0128 mole) of tedisamil were dissolved in 25 ml of ethanol. A solution of 2.98 g (=0.0256 mole) of fumaric acid in 30 ml of ethanol was added to the solution. The resulting homogeneous solution was slowly added dropwise to 500 ml of diethyl ether, and the reaction mixture was cooled in a refrigerator to complete the formation of salt. The crystals which formed were separated from the mother liquor by suction filtration, washed with 20 ml of diethyl ether, and dried in a vacuum drying oven at 60° C. 4.9 g of tedisamil 1.5 hydrogenfumarate having a melting range of 135.8 to 136.9° C. were obtained. The base:acid ratio determined by titration was 1:1.5. Thermogravimetric analysis showed no weight loss on drying.

The properties of the 1.5 hydrogenfumarates according to the invention of Examples 1 and 2 were compared with those of other salts of the same bases. Comparison Examples A-G: Preparation of comparison salts of bertosamil and tedisamil with other acids.

A) BERTOSAMIL DIHYDROGENFUMARATE 6 kg (=20.5 moles) of bertosamil were dissolved in 14.4 liters of ethanol. 4.76 kg (=41 moles) of solid fumaric acid were added to the solution. The reaction mixture was heated to 80° C. and stirred at this temperature for 30 minutes. The reaction mixture was then slowly allowed to cool to room temperature with stirring and stirred at 0° C. for a further 30 minutes in an ice bath. The precipitate which formed was separated from the mother liquor by suction filtration, washed with 10 liters of ice-cold ethanol, and dried in a drying oven at 35° C. 5.1 kg of bertosamil dihydrogenfumarate were obtained. DSC gave a melting range of 90.2 to 96.2° C. A further peak, attributed to the escape of ethanol, occurred in the temperature range from 68-81° C. Thermogravimetric analysis showed a weight loss of 7.0% on drying the salt. The base:acid ratio determined by titration was 1:2.1.

B) BERTOSAMIL DIHYDROCHLORIDE 5.4 g (-0.0154 mole) of bertosamil were dissolved in 20 ml of isopropanol. 8.2 ml of a 3.8 normal solution of hydrogen chloride in isopropanol were added to the solution with ice-cooling. The isopropanol was then removed by distillation. The residue was taken up in a little acetone and treated with diethyl ether until crystallization began. The precipitate which formed was separated from the mother liquor by suction filtration, and dried at 60° C. in a vacuum drying oven. 5 g of bertosamil dihydrochloride having a melting range of 180.6 to 183.7° C. were obtained. Thermogravimetric analysis showed a 2.0% weight loss on drying. The base:acid ratio determined by titration was 1:2.0.

C) BERTOSAMIL DIHYDROGENTARTRATE 5.4 g (=0.018 mole) of bertosamil were dissolved in 10 ml of ethyl acetate. A solution of 5.5 g (=0.037 mole) of L(+)-tartaric acid in 20 ml of acetone was added to the solution. After removal of the solvent by distillation, 8.4 g of bertosamil dihydrogentartrate were isolated as an amorphous foam. The melting range was 189.2 to 201.2° C. with decomposition. The base:acid ratio determined by titration was 1:1.8. Thermogravimetric analysis showed a 0.1% weight loss on drying.

D) BERTOSAMIL SALICYLATE 10.7 g (=0.037 mole) of bertosamil were dissolved in 40 ml of diethyl ether. A solution of 5.12 g (=0.037 mole) of salicylic acid in 30 ml of diethyl ether was added to the solution, and the reaction mixture was stirred for 30 minutes. The resulting precipitate was filtered out of the mother liquor using a suction filter, and dried at 60° C. in a vacuum drying oven. 14.5 g of bertosamil salicylate having a melting range of 118.4 to 119.5° C. were obtained. The base:acid ratio determined by titration was 1:1.0. Thermogravimetric analysis showed no weight loss on drying.

E) TEDISAMIL DIHYDROCHLORIDE 2 g (=0.0069 mole) of tedisamil were dissolved in 5 ml of isopropanol. A solution of 0.53 g of hydrochloric acid in 5 ml of isopropanol was added with stirring to this solution. After the formation of salts, isopropanol was removed by distillation, and the tedisamil dihydrochloride which remained as a residue was recrystallized from acetone and dried at 60° C. in a vacuum drying oven. 2 g of tedisamil dihydrochloride were obtained. DSC gave a melting range with decomposition at 225.7 to 240.4° C. The base:acid ratio determined by titration was 1:2.0. Thermogravimetric analysis showed a 0.2% weight loss on drying.

F) TEDISAMIL DIHYDROGENTARTRATE 3.7 g (=0.0128 mole) of tedisamil were dissolved in 15 ml of ethyl acetate. A solution of 3.85 g (=0.0256 mole) L(+)-tartaric acid in 50 ml of acetone was added to the solution. After removal of the solvent by distillation, 6 g of tedisamil dihydrogentartrate were isolated as an amorphous foam. DSC did not give a defined melting range, but decomposition from 183° C. Thermogravimetric analysis showed a 0.5% weight loss on drying. The base:acid ratio determined by titration was 1:2.1.

G) TEDISAMIL SALICYLATE 10.7 g (=0.037 mole) of tedisamil were dissolved in 50 ml of diethyl ether. A solution of 5.12 g (=0.037 mole) of salicylic acid in 50 ml of diethyl ether was added to the solution. The reaction mixture was stirred for 30 minutes. The resulting precipitate was separated from the mother liquor by suction filtration, and dried in a vacuum drying oven at 60° C. 14.5 g of tedisamil salicylate were obtained. DSC gave a melting range of 140.9 to 142.2° C. The base:acid ratio determined by titration was 1:1.0. Thermogravimetric analysis showed a 0.1% weight loss on drying.

The properties of the salts according to the invention of Examples 1 and 2 and the comparison salts of Comparison Examples A to G were determined by the following methods.

I. DETERMINATION OF THE WATER SOLUBILITY

The water solubility was determined at room temperature.

II. DETERMINATION OF THE SOLVENT RESIDUE CONTENT

The solvent residue contents were determined by means of capillary gas chromatography using a Siemens "Sicromat TM" apparatus with a flame ionization detector.

III. DETERMINATION OF THE HYGROSCOPICITY

To determine the hygroscopicity, samples of the salts were each kept at a relative atmospheric humidity of 55, 65, 76, 86, 92 and 100% at room temperature until the weight was constant. The starting weight of the samples and the weight after storage were determined gravimetrically, and the weight difference was calculated. The hygroscopicity of the substances is given as % increase in weight relative to the starting weight. In the case of substances with a solvent content, an iodometric water content determination by the Karl Fischer method was additionally carried out.

The results obtained by the experimental methods described above are shown in the following table:

TABLE

| Salt Ex. No. | H2O solubility in g/100 ml | Solvent* residue content (GC) in % by weight | | | | Hygroscopicity in % by weight increse at a relative atmospheric humidity of | | | | | |
|---|---|---|---|---|---|---|---|---|---|---|---|
| | | Et | Ac | Di | Pr | 55% | 65% | 76% | 86% | 92% | 100% |
| 1 | 4.5 | — | — | — | — | 0 | 0 | 0.04 | 0.04 | — | 0.06 |
| A** | 3.6 | 7.8 | — | — | — | −2.3 (+2.1 H2O) | −4.1 | −4.2 | −4.2 | — | −4.0 (+3.5 H2O) |
| B | >51 | — | — | — | 0.03 | 7.7 | 9.0 | 13 | 51 | — | 171 |
| C | 50 | 0.7 | 1.8 | 0.02 | — | 4.3 | 7.0 | 9.6 | 15 | — | 102 |
| D | 1.6 | — | — | — | — | 0.1 | 3.1 | 14 | 17 | — | 35 |
| 2 | 4.4 | 0.12 | — | 0.05 | — | 0 | 0 | 0 | 0 | — | 1.1 |
| E | >190 | — | — | — | 0.1 | 0.1 | 30 | 43 | 67 | 106 | — |
| F | 39 | 0.9 | 0.3 | — | — | 2.5 | 6.0 | 10 | 16 | — | 118 |
| G | 1.8 | — | — | 0.09 | — | 0 | 0.04 | 0.04 | 0.2 | — | 29 |

*ET = ethanol, Ac = acetone, Di = diethyl ether, Pr = isopropanol
**Obtained as a solvate, during storage a weight decrease takes place due to exchange of solvent for atmospheric moisture. This is reflected by the minus values given. The amount of water absorbed by the sample determined by the Karl Fischer method is given in brakets.

It is evident from this table that the 1.5 hydrogenfumarates according to the invention are virtually non-hygroscopic in contrast to the comparison salts and in spite of this have a solubility in water which is adequate for pharmaceutical purposes.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all variations falling within the ambit of the appended claims and equivalents thereof.

What is claimed is:

1. A fumaric acid salt of a 9,9-alkylene-3,7-diazabicyclo[3.3.1]nonane compound corresponding to the formula I

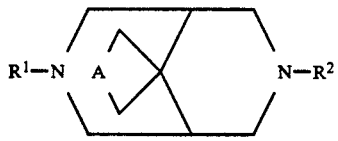

wherein
A denotes an alkylene chain of 4–5 carbon atoms, and
$R^1$ and $R^2$ independently of one another each denote a straight-chain or branched alkyl group of 3–4 carbon atoms or the cyclopropylmethyl group;
said salt containing 1.5 moles of fumaric acid per mole of compound of formula I.

2. A fumaric acid salt according to claim 1, wherein said compound of formula I is N,N'-dicyclopropylmethyl-9,9-tetramethylene-3,7-diazabicyclo[3.3.1]nonane or N-isobutyl-N'-isopropyl-9,9-pentamethylene-3,7-diazabicyclo[3.3.1]nonane.

3. N,N'-Dicyclopropylmethyl-9,9-tetramethylene-3,7-diazabicyclo[3.3.1]nonane 1.5 hydrogenfumarate according to claim 2.

4. N-Isobutyl-N'-isopropyl-9,9-pentamethylene-3,7diazabicyclo[3.3.1]nonane-1.5-hydrogenfumarate according to claim 2.

5. A pharmaceutical composition comprising an effective cardio-active amount of a fumaric acid salt according to claim 1 and at least one conventional pharmaceutical carrier or adjuvant.

6. A process for preparing a fumaric acid salt of a 9,9-alkylene-3,7-diazabicyclo[3.3.1]nonane compound corresponding to the formula I

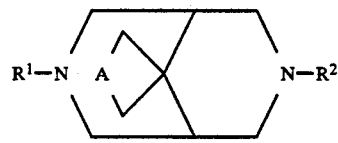

wherein
A denotes an alkylene chain of 4–5 carbon atoms, and
$R^1$ and $R^2$ independently of one another each denote a straight-chain or branched alkyl group of 3–4 carbon atoms or the cyclopropylmethyl group;
p1 said salt containing 1.5 moles of fumaric acid per mole of said compound of formula I;
said process comprising
admixing
a solution of said compound of formula I and of an at least 1.5-fold molar amount of fumaric acid in a lower alcohol, and
a less polar organic solvent,
whereby a salt containing 1.5 moles of fumaric acid per mole of said compound of formula I crystallizes, and separating the crystallized salt from the solution.

7. A process according to claim 6, wherein said less polar solvent is acetone or diethyl ether.